United States Patent [19]

Ito et al.

[11] 4,411,799

[45] Oct. 25, 1983

[54] METHOD FOR STABILIZING AN AQUEOUS SOLUTION CONTAINING A CHLORINE-BASED OXIDANT

[75] Inventors: Tomohisa Ito, Funabashi; Akira Hongo, Machida, both of Japan

[73] Assignee: Nitto Chemical Industry Co., Ltd., Tokyo, Japan

[21] Appl. No.: 340,595

[22] Filed: Jan. 19, 1982

[30] Foreign Application Priority Data

Jan. 19, 1981 [JP] Japan .................................. 56/5063

[51] Int. Cl.$^3$ ............................ C02F 5/08; C02F 1/76
[52] U.S. Cl. .................................. 210/753; 210/764; 422/37; 424/149
[58] Field of Search ............................... 210/754–756, 210/758, 764, 753; 106/15.05; 424/149, 150; 162/161; 252/181; 71/67; 422/37, 41

[56] References Cited

U.S. PATENT DOCUMENTS

| | | | |
|---|---|---|---|
| 2,583,558 | 1/1952 | Frost | 210/753 |
| 2,583,559 | 1/1952 | Frost | 210/753 |
| 3,147,219 | 9/1964 | Paterson | 210/755 |
| 3,799,758 | 3/1974 | Franz | 71/67 |
| 3,928,575 | 12/1975 | Moyle et al. | 71/67 |
| 3,930,015 | 12/1975 | Swered et al. | 71/67 |
| 4,022,605 | 5/1977 | Konya et al. | 71/67 |
| 4,297,224 | 10/1981 | Macchiarolo et al. | 210/755 |

Primary Examiner—Charles N. Hart
Assistant Examiner—Wanda L. Millard
Attorney, Agent, or Firm—Sughrue, Mion, Zinn, Macpeak & Seas

[57] ABSTRACT

A method for stabilizing an aqueous solution containing a chlorine-based oxidant is disclosed, comprising incorporating both glycine and at least one halide selected from bromide and iodide in the aqueous solution containing chlorine-based oxidant.

10 Claims, No Drawings

METHOD FOR STABILIZING AN AQUEOUS SOLUTION CONTAINING A CHLORINE-BASED OXIDANT

FIELD OF THE INVENTION

The present invention relates to a method for stabilizing an aqueous solution containing a chlorine-based oxidant, and more particularly, to a method for stabilizing an aqueous solution containing a chlorine-based oxidant by incorporating glycine and at least one halide selected from bromide and iodide in the aqueous solution.

BACKGROUND OF THE INVENTION

Chlorine, hypochlorous acid, salts thereof, chlorinated isocyanuric acids, chlorinated hydantoins and other chlorine compounds (which are hereafter collectively referred to as chlorine-based oxidants) are known to achieve very effective and quick control of aquatic growth (including bacteria) even if they are used in low concentrations. Because of their high oxidizing activity, these oxidants are used in waterworks as a sterilizer, in chemical plants and cooling towers as a sterilizer or algicide for circulated cooling water, in pulp mills as a slime control agent, and in swimming pools as a disinfectant. However, the chlorine-based oxidants in aqueous solutions do not have a long keeping quality; their oxidizing ability decreases even if they are stored at ordinary temperatures, and they are decomposed even faster by the effect of heat, light and agitating force. It therefore often occurs that the intended effect of the chlorine-based oxidants is lost in a very short time.

Sodium hypochlorite may be added to the cooling water circulating in chemical plants. Since the cooling water is heated in a heat exchanger and contacted vigorously with air in a cooling tower, the sodium hypochlorite is rapidly decomposed and its concentration is decreased to a fifth to a tenth of the initial level within a period of only 30 minutes. If the decomposition rate is slow, sodium hypochlorite having a concentration of about 1 ppm can achieve the desired sterilizing effect, but because of its rapid decomposition, it must be added in a concentration of several to several tens of ppm or it must be added at short intervals, which requires much cost and labor. For disinfecting swimming pools, the residual chlorine of chlorine-based oxidants in water should be held at from 0.4 to 2.0 ppm, but the fact is that the residual chlorine is decreased at a rate of 0.4 to 0.9 ppm per hour and thus after several hours the typical residual chlorine content is almost zero. To prevent this, the chlorine-based oxidant must be added frequently, but again, this is costly and involves much labor.

The conventional chlorine-based oxidants are more or less labile, presenting problems in their use as sterilizing agents, algicides, and disinfectants. Isocyanuric acid, a cyclic amide compound, is currently used to stabilize chlorine-based oxidants used for disinfecting water in swimming pools, but its effect is not totally satisfactory. Furthermore, since the concentration of isocyanuric acid in the water is usually about 30 ppm, the resulting waste water contains an undesirably large amount of organic matter.

To solve these problems, it is reported in, for example, Japanese Patent Application (OPI) No. 26587/81 filed by the present inventors that a use of α-amino acid is useful for stability of residual chlorine to prevent the reduction of the residual chlorine with an elapse of time (the term "OPI" as used herein refers to a "published unexamined Japanese patent application").

However, the process of Japanese Patent Application (OPI) No. 26587/81 has a defect that the strong oxidizing power of the chlorine-based oxidants used causes a significant corrosive effect on iron.

Cooling water circulating through steel-made chemical plants and cooling towers contain a corrosion inhibitor to protect the areas in contact with the cooling water, but when chlorine-based oxidants are added to the cooling water as a sterilizer or algicide, it still frequently occurs that the rate of corrosion is increased. To dislodge the slime on the inner walls of chemical plants, chlorine-based oxidants are sometimes added in a concentration of as high as several hundred to several thousand ppm, and in the presence of such high concentrations of oxidants, conventional corrosion inhibitors have only a small effect in protecting the iron.

SUMMARY OF THE INVENTION

Therefore, an object of the present invention is to overcome the problems described above by providing a method for stabilizing aqueous solutions containing chlorine-based oxidants.

Thus, the present inventors have made extensive studies to develop a method for stabilizing aqueous solutions containing chlorine-based oxidants so as to enhance their effect to kill microorganisms and inhibit the corrosive effect of these oxidants.

As a result, it has now been found that this objective can be achieved by incorporating both glycine and at least one halide selected from a bromide and iodide in the aqueous solution containing chlorine-based oxidant.

Glycine itself is effective to prevent the significant reduction in the oxidizing ability of the aqueous solutions containing chlorine-based oxidants, and it effectively retains their ability to control aquatic growths, but it has substantially no capability of inhibiting iron corrosion.

Bromides and iodides are not only unable to prevent the reduction in the oxidizing ability of the aqueous solutions containing chlorine-based oxidants, but also they have no ability to inhibit iron corrosion. However, unexpectedly, it has been found that by using glycine and at least one halide selected from bromide and iodide at the same time, the active oxygen of chlorine-based oxidants is stabilized, and the ability of aqueous solutions containing chlorine-based oxidants to control aquatic growths becomes greater than when glycine is used alone, and, at the same time, iron corrosion is greatly reduced.

DETAILED DESCRIPTION OF THE INVENTION

Aqueous solutions which can be treated by the method of the invention includes those which contain chlorine-based oxidants such as chlorine, hypochlorous acid, salts thereof such as sodium, potassium, and calcium salts, chlorinated isocyanuric acids such as isocyanuric trichloride, dichloride, and salts thereof such as sodium and potassium salts, and chlorinated hydantoins such as 1,3-dichloro-5,5-dimethylhydantoin.

Bromides that can be used in the method of the present invention include sodium bromide, potassium bromide, calcium bromide, magnesium bromide, etc., and iodides that can be used include sodium iodide, potassium iodide, calcium iodide, magnesium iodide, etc.

According to the present invention, the glycine and bromides and/or iodides may be added to aqueous solutions containing chlorine-based oxidants; or chlorine-based oxidants may be added to aqueous solutions containing the glycine and bromides and/or iodides; or chlorine-based oxidants, the glycine and the bromides and/or iodides may be added to water at the same time. The weight ratio of glycine to the bromide, iodide, or bromide/iodide is preferably in the range of from 1:9 to 9:1, more preferably from 2:8 to 8:2. The sum of the bromide, iodide, bromide/iodide and glycine to be added in the aqueous solutions is preferably at least 1.0 ppm by weight, more preferably 1.0 to 15 ppm, and most preferably 2.0 to 10 ppm.

According to the method of the present invention, the reduction in the oxidizing power of the chlorine-based oxidants can be suppressed and their sterilizing, algicidal, and disinfecting effects can be prolonged by simply incorporating glycine and at least one halide selected from bromide and iodide in the solutions. Therefore, the frequency or amount of addition of the chlorine-based oxidants can be reduced with advantage as to economy.

The method of the present invention is also effective in inhibiting corrosion of iron by chlorine-based oxidants, which is very difficult to prevent by conventional corrosion inhibitors. For example, by using the present invention, heat exchangers in the system of circulating cooling water through a chemical plant are effectively protected from corrosion and their life can be extended remarkably.

As a further advantage, the bromides and iodides used as well as glycine in the present invention present substantially no health hazards, because the former are typical components of seawater, and the latter is a common food additive. Therefore, the present invention offers an economical and safe method for stabilizing the aqueous solutions containing chlorine-based oxidants.

The present invention is now described in greater detail by reference to the following examples and comparative examples which are given here for illustrative purposes only, and are not intended to limit its scope.

EXAMPLES 1 TO 8 AND COMPARATIVE EXAMPLES 1 TO 8

Glycine, potassium bromide and potassium iodide were added to water (35° C.) in the amounts indicated in Table 1. To the solution, a 12 wt% aqueous solution of sodium hypochlorite was added so that the concentration of sodium hypochlorite was 3.5 ppm. The resulting solution was agitated at 200 rpm (35° C., pH: 7.4), then the changes with the elapse of time (each of 1, 2, 3 and 4 hours) in the concentration of active oxygen in the solution were measured by an iodometric titration method. The results are shown in Table 1 below. As controls, four samples were prepared (Comparative Examples 1 to 4); one was an aqueous solution of sodium hypochlorite containing no additive; the other sodium hypochlorite solutions contained only glycine, potassium bromide, and potassium iodide, respectively, in the amounts indicated in Table 1.

Further, in order to demonstrate that glycine is most preferred among α-amino acids, the samples were prepared in the same procedure as in the above examples except that DL-alanine, sodium glutamate, methionine and aspartic acid in the amounts indicated in Table 1 were added instead of glycine (Comparative Examples 5 to 8). The results are shown in Table 1 below.

TABLE 1

| | Additive (ppm) | | | | Active Oxygen (ppm) | | | |
|---|---|---|---|---|---|---|---|---|
| | α-Amino Acid | Glycine | Potassium Bromide | Potassium Iodide | 1 Hr | 2 Hr | 3 Hr | 4 Hr |
| Comparative Example 1 | — | 0 | 0 | 0 | 1.0 | 0.35 | 0.2 | 0.15 |
| Comparative Example 2 | — | 2.5 | 0 | 0 | 1.5 | 1.1 | 0.6 | 0.4 |
| Comparative Example 3 | — | 0 | 5.0 | 0 | 0.5 | 0.3 | 0.2 | 0.3 |
| Comparative Example 4 | — | 0 | 0 | 5.0 | 0.7 | 0.5 | 0.3 | 0.2 |
| Comparative Example 5 (DL-alanine) | 5.0 | — | 5.0 | 0 | 1.25 | 1.0 | 0.75 | 0.4 |
| Comparative Example 6 (sodium glutamate) | 5.0 | — | 5.0 | 0 | 1.25 | 1.0 | 0.5 | 0.25 |
| Comparative Example 7 (methionine) | 5.0 | — | 5.0 | 0 | 0.5 | 0.25 | 0.25 | 0.1 |
| Comparative Example 8 (aspartic acid) | 5.0 | — | 5.0 | 0 | 1.25 | 0.75 | 0.25 | 0.25 |
| Example 1 | — | 2.5 | 2.0 | 0 | 1.5 | 1.5 | 1.25 | 1.1 |
| Example 2 | — | 5.0 | 2.0 | 0 | 1.5 | 1.5 | 1.25 | 1.1 |
| Example 3 | — | 10 | 2.0 | 0 | 1.5 | 1.5 | 1.25 | 1.1 |
| Example 4 | — | 2.5 | 5.0 | 0 | 1.5 | 1.25 | 1.0 | 0.6 |
| Example 5 | — | 5.0 | 5.0 | 0 | 1.5 | 1.5 | 1.25 | 1.1 |
| Example 6 | — | 10 | 5.0 | 0 | 1.25 | 1.25 | 0.8 | 0.5 |
| Example 7 | — | 5.0 | 0 | 5.0 | 1.5 | 1.5 | 1.25 | 1.25 |
| Example 8 | — | 5.0 | 2.5 | 2.5 | 1.5 | 1.5 | 1.0 | 0.8 |

EXAMPLE 9 AND COMPARATIVE EXAMPLES 9 TO 11

A sample was prepared and the change in the concentration of active oxygen was measured in the same procedure as in Examples 1 to 8 and Comparative Examples 1 to 8, except that the 12 wt% aqueous solution of sodium hypochlorite was replaced by 3.5 wt% aqueous solution of sodium dichloroisocyanurate. Three controls were prepared; one was an aqueous solution of sodium dichloroisocyanurate, and the other sodium dichloroisocyanurate solutions contained only glycine and potassium bromide, respectively. The results are shown in Table 2 below.

TABLE 2

| | Additive (ppm) | | Active Oxygen (ppm) | | | |
|---|---|---|---|---|---|---|
| | Glycine | Potassium Bromide | 1 Hr | 2 Hr | 4 Hr | 6 Hr |
| Comparative Example 9 | 0 | 0 | 0.7 | 0.5 | 0.2 | 0 |
| Comparative Example 10 | 4.0 | 0 | 1.5 | 1.0 | 0.8 | 0.4 |
| Comparative Example 11 | 0 | 6.0 | 0.8 | 0.4 | 0.3 | 0 |
| Example 9 | 4.0 | 6.0 | 1.5 | 1.25 | 1.0 | 0.5 |

EXAMPLE 10 AND COMPARATIVE EXAMPLES 12 TO 14

To a cooling water system in a plant for methylamine production (retained water: 400 ton, circulating water: 2,500 ton/hr, temperature of water at inlet of heat exchanger: 20.5° C., temperature at outlet: 40° C., pH: 7.3), glycine and potassium bromide were added in the amounts indicated in Table 3. To the solutions, sodium hypochlorite was added to provide a concentration of 12 ppm. As in Example 1, the change in the concentration of active oxygen was checked. The change in the number of live cells with elapse of time was also measured by calculating the number of colonies of bacteria (in 1 ml of sample) grown on the culture media at 35° C. Three controls were prepared: one was an aqueous solution of sodium hypochlorite containing neither glycine nor potassium bromide, and the other sodium hypochlorite solutions contained glycine and potassium bromide, respectively. The results are shown in Tables 3-a and 3-b.

TABLE 3-a

| | Additive (ppm) | | Active Oxygen (ppm) | | | | |
|---|---|---|---|---|---|---|---|
| | Glycine | Potassium Bromide | 1 Hr | 2 Hr | 4 Hr | 7 Hr | 24 Hr |
| Comparative Example 12 | 0 | 0 | 0.35 | 0.1 | 0 | 0 | 0 |
| Comparative Example 13 | 0 | 6 | 0.2 | 0.1 | 0 | 0 | 0 |
| Comparative Example 14 | 10 | 0 | 3.5 | 2.5 | 0.7 | 0.1 | 0 |
| Example 10 | 4 | 6 | 3.8 | 2.8 | 1.0 | 0.3 | 0.05 |

TABLE 3-b

| | Additive (ppm) | | Live Cells ($\times 10^3$/ml) | | | | |
|---|---|---|---|---|---|---|---|
| | Glycine | Potassium Bromide | 0 Hr | 1 Hr | 7 Hr | 24 Hr | 48 Hr |
| Comparative Example 12 | 0 | 0 | 45 | 0 | 4.0 | 20 | 50 |
| Comparative Example 13 | 0 | 6 | 46 | 0 | 4.2 | 25 | 48 |
| Comparative Example 14 | 10 | 0 | 45 | 0 | 1.3 | 3.8 | 40 |
| Example 10 | 4 | 6 | 47 | 0 | 0.2 | 2.5 | 20 |

As shown in Table 3, the oxidizing power of sodium hypochlorite was effectively maintained by the addition of glycine and potassium bromide, and the increase in the number of live cells was slower than when only glycine was used.

EXAMPLES 11 AND 12 AND COMPARATIVE EXAMPLES 15 TO 20

To the water sampled from a cooling water system in a plant for methylamine production, glycine, potassium bromide and sodium hypochlorite were added in the amounts indicated in Table 4. The so-prepared test liquors were adjusted to a pH of 7.5 and held at 40° C. Test pieces made of soft steel plate (JIS G 3141 steel plate, Steel Plate Cold Commercial "SPCC") was mounted on the tip of revolving shafts in jar testers filled with the test liquors and were revolved at 150 rpm. The test liquors were replaced with a new specimen thereof every other day. On the 8th day, the corrosion rate was determined from the weight loss of the test piece. Three controls were prepared: one was an aqueous solution of sodium hypochlorite, and the other sodium hypochlorite solutions contained only glycine and potassium bromide, respectively. The results are set forth in Table 4. The rate of corrosion was indicated by "mdd" which means the weight (mg) of the test piece that was corroded for a unit area of 100 cm$^2$ per day.

TABLE 4

| | Sodium Hypochlorite (ppm) | Additive (ppm) | | Corrosion Rate (mdd) |
|---|---|---|---|---|
| | | Glycine | Potassium Bromide | |
| Comparative Example 15 | 10 | 0 | 0 | 17 |
| Comparative Example 16 | 10 | 4.0 | 0 | 14 |
| Comparative Example 17 | 10 | 0 | 6.0 | 12 |
| Example 11 | 10 | 4.0 | 6.0 | 1.5 |
| Comparative Example 18 | 100 | 0 | 0 | 189 |
| Comparative Example 19 | 100 | 4.0 | 0 | 126 |
| Comparative Example 20 | 100 | 0 | 6.0 | 192 |
| Example 12 | 100 | 4.0 | 6.0 | 49 |

As is clear from Table 4, the method of the present invention is very effective in inhibiting corrosion of iron by hypochlorites.

While the invention has been described in detail and with reference to specific embodiments thereof, it will be apparent to one skilled in the art that various changes and modifications can be made therein without departing from the spirit and scope thereof.

What is claimed is:

1. A method for stabilizing an aqueous solution containing a chlorine-based oxidant comprising both glycine and at least one halide in a weight ratio of 1:9 to 9:1 with the halide selected from bromide and iodide in the solution.

2. A method according to claim 1, wherein the chlorine-based oxidant is at least one compound selected from the group consisting of chlorine, hypochlorous acid, a salt thereof, a chlorinated isocyanuric acid, and a chlorinated hydantoin.

3. A method according to claim 1 or 2, wherein the bromide is sodium bromide, potassium bromide, calcium bromide, or magnesium bromide, and the iodide is sodium iodide, potassium iodide, calcium iodide or magnesium iodide.

4. A method according to claim 1 or 2, wherein weight ratio of glycine to halide is from 2:8 to 8:2.

5. A method according to claim 1, wherein the sum of the glycine and halide content incorporated in the solution is at least 1.0 ppm by weight.

6. A method according to claim 5, wherein the sum of the glycine and halide content incorporated in the solution is 1.0 to 15 ppm by weight.

7. A method according to claim 6, wherein the sum of the glycine and halide content incorporated in the solution is 2.0 to 10 ppm by weight.

8. A stabilized aqueous solution of a chlorine-based oxidant, comprising glycine and at least one halide selected from bromide and iodide.

9. A stabilized solution according to claim 8, wherein the chlorine-based oxidant is at least one compound selected from the group consisting of chlorine, hypochlorous acid, a salt thereof, a chlorinated isocyanuric acid, and a chlorinated hydantoin.

10. A stabilized solution according to claim 8 or 9, wherein the bromide is sodium bromide, potassium bromide, calcium bromide, or magnesium bromide, and the iodide is sodium iodide, potassium iodide, calcium iodide or magnesium iodide.

* * * * *